(12) United States Patent
Poshusta et al.

(10) Patent No.: US 9,284,268 B2
(45) Date of Patent: Mar. 15, 2016

(54) SYNTHESIS OF FLUOROTRIFLUOROMETHYLSULFONYL IMIDE

(71) Applicants: Joseph Carl Poshusta, Broomfield, CO (US); Jerry Lynn Martin, Superior, CO (US); Rajendra P. Singh, Broomfield, CO (US)

(72) Inventors: Joseph Carl Poshusta, Broomfield, CO (US); Jerry Lynn Martin, Superior, CO (US); Rajendra P. Singh, Broomfield, CO (US)

(73) Assignee: CoorsTek Fluorochemicals, Inc., Arvada, CO (US)

( * ) Notice: Subject to any disclaimer, the term of this patent is extended or adjusted under 35 U.S.C. 154(b) by 11 days.

(21) Appl. No.: 14/071,597

(22) Filed: Nov. 4, 2013

(65) Prior Publication Data

US 2015/0126778 A1    May 7, 2015

(51) Int. Cl.
*C07C 303/40*    (2006.01)

(52) U.S. Cl.
CPC .................. *C07C 303/40* (2013.01)

(58) Field of Classification Search
CPC .................. C07C 303/38; C07C 303/40
USPC ................... 564/82, 83; 562/822
See application file for complete search history.

(56) References Cited

FOREIGN PATENT DOCUMENTS

RU    2183621    *    6/2002    ........... C07C 309/80

OTHER PUBLICATIONS

Beran et al., "A new route to the syntheses of N-(fluorosulfuryl)sulfonamide salts: Crystal structure of Ph4P+[CF3SO2NSO2]-," Polyhedron 29 (2010) 991-994.*
English Translation of RU2183621, pp. 1-8.*

* cited by examiner

*Primary Examiner* — Paul A Zucker
*Assistant Examiner* — Mark Luderer
(74) *Attorney, Agent, or Firm* — Don D. Cha, Esq.; Hamilton DeSanctis & Cha, LLP.

(57) ABSTRACT

The invention provides a method for producing fluorotrifluoromethylsulfonyl imide (FTFSI) by reacting non-fluorohalogenated trihalomethylsulfonyl imide (XTXSI) with hydrogen fluoride, where each X is independently a nonfluoro-halide, such as Cl, Br, or I.

18 Claims, 1 Drawing Sheet

# US 9,284,268 B2

SYNTHESIS OF FLUOROTRIFLUOROMETHYLSULFONYL IMIDE

FIELD OF THE INVENTION

The present invention relates to a method for producing fluorotrifluoromethylsulfonyl imide (FTFSI) from halotrihalomethylsulfonyl imide (i.e., "XTXSI", where X is non-fluoro-halide) using hydrogen fluoride.

BACKGROUND OF THE INVENTION

Fluorotrifluoromethylsulfonyl imide (FTFSI) is useful in various applications including electrolytes in electrochemical devices such as batteries and capacitors and as an ionic liquid component.

Despite the usefulness of FTFSI, no commercial production process for producing FTFSI exists.

Accordingly, there is a need for a simple method for producing a high yield of FTFSI.

SUMMARY OF THE INVENTION

One aspect of the invention provides a method for producing fluorotrifluoromethylsulfonyl imide (FTFSI) from a non-fluoro halogenated trihalomethylsulfonyl imide (i.e., halotrihalomethylsulfonyl imide or XTXSI) compound of the formula:

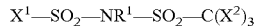

$$X^1\text{—}SO_2\text{—}NR^1\text{—}SO_2\text{—}C(X^2)_3 \qquad \text{I}$$

where
  $X^1$ is non-fluoro halide;
  each of $X^2$ is independently halide; and
  $R^1$ is hydrogen, alkyl, or a nitrogen protecting group.
Typically, the method of invention comprises reacting the non-fluoro halogenated trihalomethylsulfonyl imide compound (XTXSI) with hydrogen fluoride under conditions sufficient to produce FTFSI.

Unlike many fluorination reaction, the method of the invention does not require a high pressure reaction system. However, it should be appreciated that the scope of the invention includes using a high pressure, high temperature or both.

In one embodiment, said reacting step also produces $HX^1$, $HX^2$, or a combination thereof. Within this embodiment, in some instances, said step of reacting said non-fluoro halogenated trihalomethylsulfonyl imide compound with hydrogen fluoride also comprises removing $HX^1$, $HX^2$ or a combination thereof.

Yet in another embodiment, said reaction condition comprises hydrogen fluoride refluxing condition. Within this embodiment, in some instances, said reaction condition comprises an ambient pressure condition.

In one particular embodiment, $X^1$ and $X^2$ are Cl.

Still in another embodiment, the reaction temperature is at least 30° C.

Yet in another embodiment, at least 2 equivalent of total hydrogen fluoride relative to said non-fluoro halogenated trihalomethylsulfonyl imide compound is added to the reaction.

In yet another embodiment, the yield of FTFSI is at least 90%.

In some embodiments, said reaction condition comprises the presence of a catalyst. Within these embodiments, in some instances said catalyst comprises a Lewis acid. In some cases, said Lewis acid comprises a salt of an alkaline metal, arsenic, antimony, bismuth, zinc, or a combination thereof. In one particular embodiment, said Lewis acid is a salt of Bi(III) compound. Yet in another embodiment, about 0.5 equivalent or less of said catalyst is added to the reaction.

Still in another embodiment, the method of the invention further comprises the step of producing said non-fluoro halogenated trihalomethylsulfonyl imide compound. Such a step typically includes:
  contacting sulfamic acid with thionylhalide of the formula:
    $SO(X^1)_2$ under conditions sufficient to produce a reactive intermediate, wherein each $X^1$ is non-fluoro halide; and
  contacting the reactive intermediate with a trihalomethanesulfonic acid of the formula:
    $(X^2)_3SO_3H$ under conditions sufficient to produce said non-fluoro halogenated trihalomethylsulfonyl imide, wherein each $X^2$ is independently a non-fluoro halide.
In some instances, $X^1$ is chloro. Yet in other instances, $X^2$ is chloro.

In some embodiments, $R^1$ of Formula I is hydrogen.

DETAILED DESCRIPTION OF THE INVENTION

Figure 1:
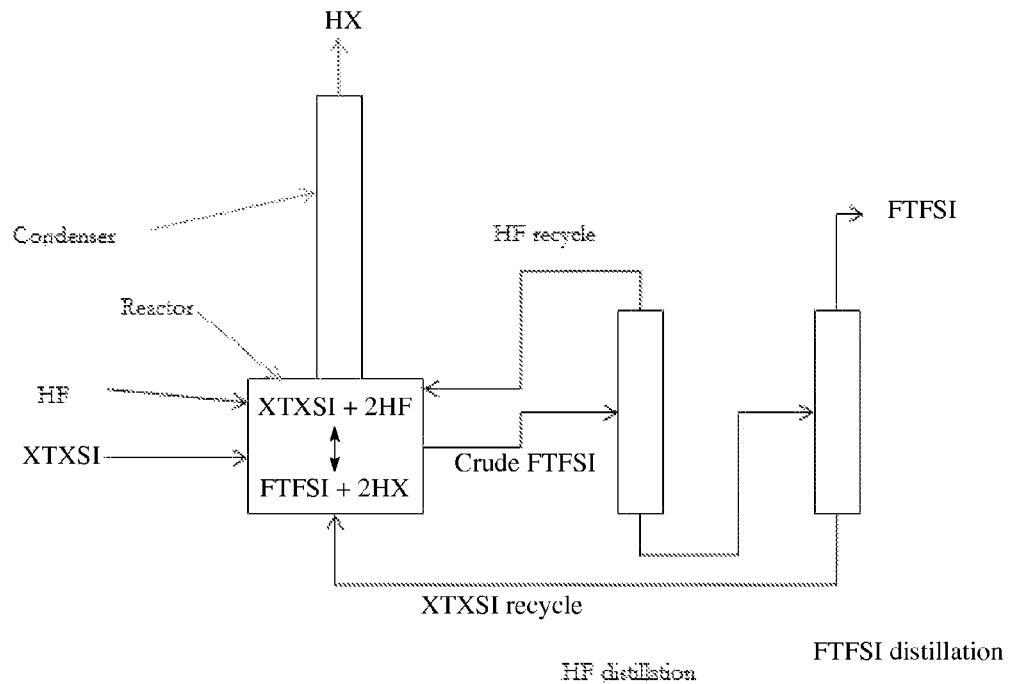
FIG. 1 is a schematic illustration of one particular embodiment of a continuous CSTR for FTFSI synthesis with distillation and recycle.

One aspect of the invention provides a method for producing fluorotrifluoromethylsulfonyl imide (FTFSI) from a halotrihalomethylsulfonyl imide (XTXSI) compound using hydrogen fluoride. The halotrihalomethylsulfonyl imide (XTXSI) compound is of the formula:

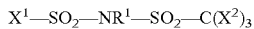

$$X^1\text{—}SO_2\text{—}NR^1\text{—}SO_2\text{—}C(X^2)_3 \qquad \text{I}$$

where
  $X^1$ is non-fluoro halide;
  each of $X^2$ is independently halide; and
  $R^1$ is hydrogen, alkyl, or a nitrogen protecting group;
The method of invention includes reacting the XTXSI compound with hydrogen fluoride (HF) under conditions sufficient to produce FTFSI.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

In one embodiment, the reaction typically produces $HX^1$, $HX^2$, or a combination thereof. Because these $HX^1$ and $HX^2$ are typically gases having a boiling point or a vapor pressure lower than HF used in the reaction, they can be readily removed preferentially relative to HF. For example, $HX^1$ and $HX^2$ can be removed from the reaction mixture by distillation or evaporation. Any HF that may evaporate or distill during the process of removing $HX^1$ and $HX^2$ can be condensed and returned back into the reaction mixture. The use of a condenser to condense HF back into the reaction mixture reduces the amount of HF required to produce FTFSI. Generally, by adjusting the condensation temperature, one can selectively condense HF while allowing $HX^1$ and $HX^2$ to be distilled away from the reaction mixture. For example, by adjusting the condensation temperature, using ice-water or dry ice and a solvent, one can condense HF to liquid while maintaining $HX^1$ and $HX^2$ to remain as a gas, which can be easily removed, e.g., by allowing it to escape the reaction mixture and trapping the gaseous $HX^1$ and $HX^2$ or by reacting the $HX^1$ and $HX^2$ generated with a base.

Because $HX^1$ and $HX^2$ that are produced in the reaction are corrosive, one can capture distilled $HX^1$ and $HX^2$ by allowing the distilled $HX^1$ and $HX^2$ to pass through another condenser at a temperature that is sufficiently low enough to allow $HX^1$ and $HX^2$ to be captured. Alternatively, $HX^1$ and $HX^2$ can be neutralized by reacting with a base including, but not limited to, a hydroxide, a bicarbonate or a carbonate. Exemplary bases that can be used to neutralize $HX^1$ and $HX^2$ include, but are not limited to, sodium hydroxide, potassium hydroxide, magnesium hydroxide, calcium hydroxide, lithium hydroxide, sodium carbonate, sodium bicarbonate, lithium bicarbonate, calcium bicarbonate, magnesium bicarbonate, potassium bicarbonate, sodium carbonate, lithium carbonate, potassium carbonate, calcium carbonate, magnesium carbonate, etc. Alternatively, $HX^1$ and $HX^2$ can be captured in water to yield an aqueous acid.

The boiling point of HF at 1 atmospheric pressure is 19.5° C. Thus, HF is a gas at the standard conditions (i.e., 1 atmosphere of pressure at 20° C.). Thus, generally the use of HF in a reaction often requires a pressure vessel in order to prevent HF from escaping the reaction mixture. Such use of a pressure vessel is inconvenient, creates a potentially dangerous condition, and reduces the commercial applicability of production of a large scale FTFSI. Accordingly, to avoid such inconvenience and potentially dangerous conditions, in some embodiments, the method of invention uses an ambient pressure condition without the need for a pressure vessel.

Due to a relatively low boiling point of HF, most, if not all, reactions involving the use of HF utilized a pressurized reaction vessel. Such use of a pressurized reaction vessel kept all the reactants and products within the reaction vessel until the reaction was stopped. In contrast, the method of the invention typically utilizes an ambient (e.g., atmospheric) pressure condition. Without being bound by any theory, it is believed that removing $HX^1$ and $HX^2$ as they are generated during the reaction increases the yield of FTFSI in accordance with the Le Chatelier's Principle.

The method of the invention includes adding HF batch-wise. In a batch-wise addition, typically HF is added in a gaseous form all at once or in portions and is allowed to condense back into the reaction mixture via a condenser. Alternatively, the reaction can be conducted by adding HF continually or continuously until a desired amount of HF has been added. Still alternatively, HF can be added substantially all at once, e.g., as fast as the desired amount of HF condensation can be achieved. Typically, however, HF is continuously added or added in a controlled manner throughout the reaction time at a substantially constant temperature.

The amount of HF added to the reaction is at least 1 equivalent compared to the amount of XTXSI added. It should be appreciated that theoretically one mole of XTXSI requires 4 moles of HF to produce the desired FTFSI. Accordingly, 1 equivalent of HF is equal to four times the number of moles of XTXSI used. For example, if 1 mole of XTXSI is used, then 1 equivalent of HF is 4 moles of HF. Because there can be some loss of HF in the reaction, typically the total amount of HF added is more than 1 equivalent, often at least 1.5 equivalent, more often at least 2 equivalents, and still more often at least 2.5 equivalents.

The reaction temperature for methods of the invention is at least that of the boiling point of $HX^1$ and $HX^2$ that is produced. In this manner, $HX^1$ and $HX^2$ that is produced can be easily removed from the reaction mixture by distillation or evaporation or as described herein. Since the boiling point of HF is higher than $HX^1$ or $HX^2$, any HF that is also evaporated or distilled can be condensed back into the reaction mixture by using a condenser of appropriate temperature. Typically, the reaction temperature is at least 30° C., often at least 60° C., and more often at least 100° C.

It has been found by the present inventors that under certain reaction conditions, reacting HF with XTXSI resulted in formation of FTFSI in at least 80% yield, typically in at least 85% yield, often at least 90% yield and more often at least 95% yield.

While not necessary, in some embodiments, methods of the invention include adding a catalyst. In particular, in some instances, XTXSI is reacted with HF in the presence of a catalyst. Suitable catalysts for methods of the invention include, but are not limited to, Bi(III) compounds, such as $BiCl_3$, $BiF_3$, and Sb(III) compounds such as $SbCl_3$ and $SbF_3$, and As(III) compounds such as $AsCl_3$ and $AsF_3$. Within these embodiments, in some instances, the catalyst comprises a Bi(III) compound. In some cases, the catalyst is a bismuth trihalide compound, such as $BiCl_3$ and $BiF_3$.

When a catalyst is used, typically about 0.5 equivalent or less, often 0.2 equivalent or less, and more often 0.1 equivalent or less relative to the total initial amount of HXSI is added to the reaction.

One particular aspect of the invention provides a process for producing hydrogen bis(fluorosulfonyl)imide (HFSI) from hydrogen bis(chlorosulfonyl)imide (HCSI) in at least 80% yield. The process of this aspect of the invention comprises: reacting HCSI with HF under conditions sufficient to reflux HF and selectively removing hydrochloric acid (HCl) that is formed in the reaction.

In one particular embodiment, the reaction condition comprises atmospheric pressure.

Yet in another embodiment, chlorotrichloromethylsulfonyl imide (CTCSI) is reacted with HF in the absence of or in the presence of a catalyst. Suitable catalysts are those disclosed herein and include bismuth trichloride and bismuth trifluoride.

CTCSI can be produced by any of the methods known to one skilled in the art. For example, CTCSI can be produced by the following reaction:

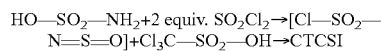

Thus, reacting at least 2 equivalents of thionyl chloride with sulfamic acid produces an isothiocyanate intermediate. Reacting this intermediate with trichloromethanesulfonic acid then produces the desired CTCSI.

In some embodiments, the reaction is conducted in a continuous stirred tank reactor with continuous XTXSI and HF feeds. In some instances, the crude product stream is distilled to recover purified FTFSI. Any unreacted XTXSI and HF that may be present can be recycled back into the reactor.

It should be appreciated that in a reaction shown below involving exchange of a nonfluorohalide (such as chlorine) with a fluorine atom, an equilibrium between forward and reverse reactions can limit the conversion to the desired exchanged product.

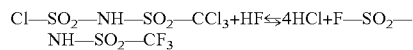

According to the Le Chatelier's Principle, selective removal of the HCl product in this reaction, shifts equilibrium to the right hand side thereby producing more of the desired FTFSI. Whereas a reaction of CTCSI with HF in a sealed vessel is expected to favor the left-side of the reaction due to a higher resulting pressure (i.e., 4 equivalents of HCl compared to 1 equivalents of HF) of the right-side of the reaction. By removing HCl that is produced from the reaction mixture and selectively condensing and returning HF back into the reaction mixture, the method of the invention allows higher yield of FTFSI compared to a reaction condition under high pressure (e.g., >>1 atmospheric pressure). It should be noted that instead of distillation or boiling, one can alternatively use a membrane separation, extraction, adsorption, ion exchange and other separation methods to selectively remove HCl from the reaction mixture. Alternatively, a combination of these gas separation methods can also be used.

A catalyst can act to increase the equilibrium and/or the rate of reaction so that the reaction proceeds more quickly at a specific temperature. It should be appreciated, however, the reaction does not require a catalyst to give acceptable results. In some instances, it was shown that the catalyst enhances reaction rate significantly at about 60° C. At 100° C., the catalytic effect was relatively smaller.

The invention may be conducted in either a batch-wise or continuous fashion. In a batch-wise approach, a reactor is loaded with CTCSI, HF and optionally catalyst, and then the HF is refluxed until HCl is completely removed. In practice, the refluxing temperature of the reaction mixture strongly depends on the amount of unreacted HF in the reactor. In general, a higher HF concentration results in a lower reaction refluxing temperature. Thus, in order to maintain a sufficiently high reaction temperature, HF is added gradually during the reaction to prevent the amount of excess HF at any given time from being too high to achieve the desired reaction temperature. The normal boiling point of pure HF is near room temperature (19.5° C.), and those of both CTCSI and FTFSI are well above 100° C. HCl is a gas at room temperature with a normal boiling point of −85° C.

The reaction refluxing temperature can be used to monitor the progress of reaction. Typically, as HF is consumed, the reaction refluxing temperature increases. Carefully metering the HF feed rate can also be used to maintain a relatively constant reaction temperature. The HF feed rate to maintain a constant reaction temperature can also indicate the reaction rate. The reaction is completed when the feed rate drops to zero at the reaction temperature.

Figure 2:
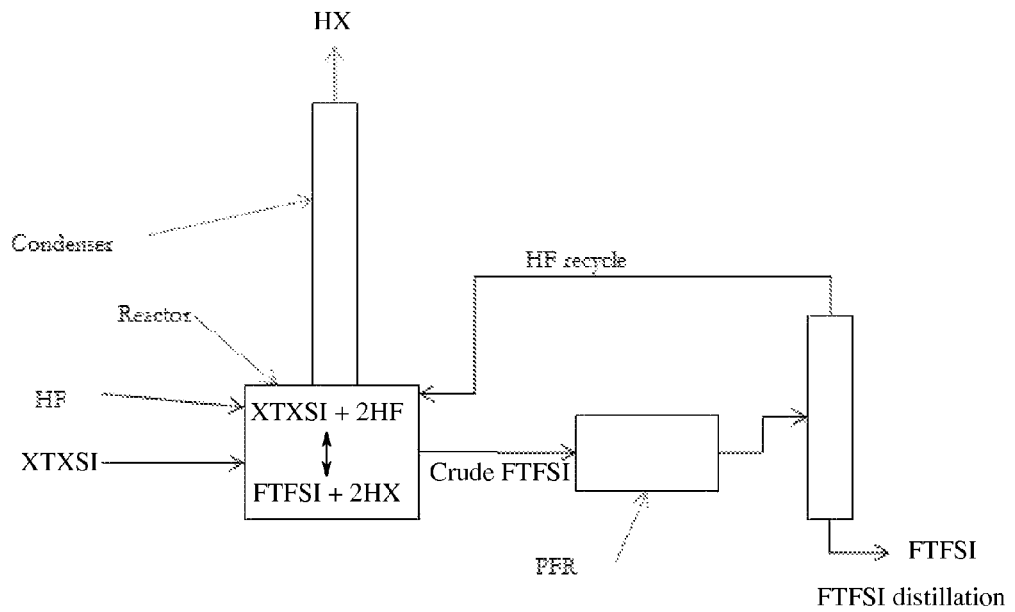
FIG. 2 is a schematic illustration of one particular embodiment of a continuous FTFSI production reactor system.

In continuous operation, a continuous stirred tank reactor (CSTR) is advantageous as it allows HF refluxing and continuous HCl removal. By design, a CSTR cannot operate at complete conversion, and therefore, the product from the reactor is crude and has residual HF and CTCSI. The FTFSI product can be purified by two stage distillation to remove volatile HF and the high boiling CTCSI. The recovered HF and CTCSI can be recycled back into the CSTR. See FIG. 1. The second stage distillation is advantageously operated under vacuum (e.g., 10-30 torr) in order to avoid thermal degradation of the FTFSI product. Alternatively, a plug flow reactor (PFR) may follow the CSTR, where the unreacted CTCSI is completely converted to FTFSI. See FIG. 2. In this configuration, only a single distillation column or gas stripping column is required to remove volatile HCl and recover HF. Again, the recovered HF can be recycled by returning it back to the CSTR.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1

This example illustrates synthesis of $CF_3SO_2NHSO_2F$ by the reaction of trifluoromethane sulfonamide ($CF_3SO_2NH_2$), thionyl chloride ($SOCl_2$), chlorosulfonic acid ($ClSO_3H$) to produce $CF_3SO_2NHSO_2Cl$ intermediate, which is then fluorinated with anhydrous hydrogen fluoride (HF) to produce $CF_3SO_2NHSO_2F$.

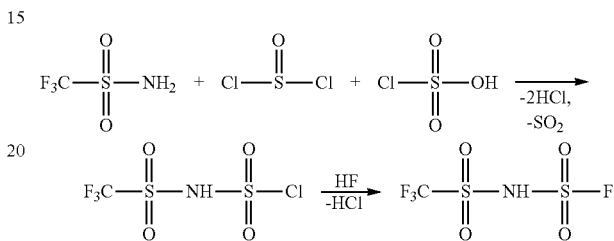

A three neck dry round bottom flask equipped with a water condenser, argon line adapter, stir bar, and a thermometer is charged with trifluoromethane sulfonamide (9.08 g, 0.061 mole), thionyl chloride (10.70 g, 6.56 ml, 0.09 mole), and chlorosulfonic acid (7.10 g, 4.05 ml, 0.061 mole). The resulting mixture is heated with oil bath to temperature of 125° C. and is stirred for 15 h. The released HCl and $SO_2$ gases are scrubbed with aqueous KOH solution. The resulting mixture is concentrated at 50° C. under reduced pressure using liquid nitrogen trap for 1 h to obtain $CF_3SO_2NHSO_2Cl$ in almost quantitative yield. This intermediate is transferred to a Teflon reactor under argon atmosphere and is treated with anhydrous HF (0.2 mole) at 100° C. under refluxing condition for 5 h. The excess HF and HCl that is generated are removed under the flow of argon at higher temperature and scrubbed with aqueous KOH solution. The crude product is distilled at reduced pressure to afford $CF_3SO_2NHSO_2F$ in good yield.

Example 2

This example illustrates synthesis of $CF_3SO_2NHSO_2F$ by the reaction of trifluoromethane sulfonamide ($CF_3SO_2NH_2$), thionyl chloride ($SOCl_2$) and fluorosulfonic acid ($FSO_3H$).

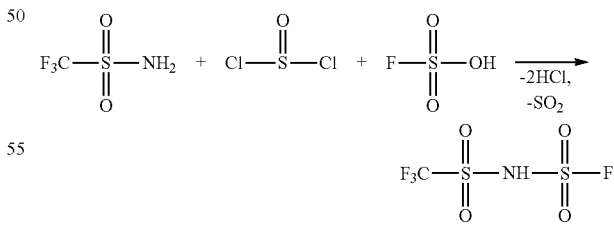

A three neck dry round bottom flask equipped with a condenser, argon line adapter, stir bar, and a thermometer is charged with trifluoromethane sulfonamide (8.00 g, 0.054 mole), thionyl chloride (10.12 g. 6.20 ml, 0.085 mole), and fluorosulfonic acid (5.40 g, 3.93 ml, 0.054 mole). The resulting mixture is heated with oil bath to temperature of 120° C. and is stirred for 20 h. The released HCl and $SO_2$ gases are scrubbed with aqueous KOH solution. The obtained crude product is distilled at reduced pressure to afford $CF_3SO_2NHSO_2F$ in very good yield.

Example 3

This example illustrates synthesis of $CF_3SO_2NHSO_2F$ by the reaction of trichloromethane sulfonamide ($CCl_3SO_2NH_2$), thionyl chloride ($SOCl_2$), chlorosulfonic acid ($ClSO_3H$) to produce $CCl_3SO_2NHSO_2Cl$ intermediate, and fluorinating the intermediate with anhydrous hydrogen fluoride (HF) to produce $CF_3SO_2NHSO_2F$.

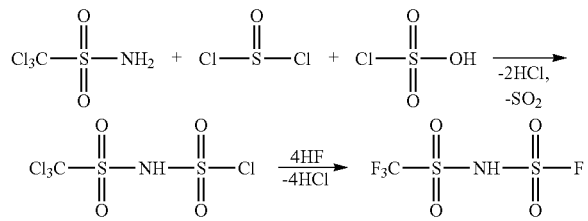

A three neck dry round bottom flask equipped with a water condenser, argon line adapter, stir bar, and a thermometer is charged with trichlororomethane sulfonamide (12.11 g, 0.061 mole), thionyl chloride (10.70 g, 6.56 ml, 0.09 mole), and chlorosulfonic acid (7.10 g, 4.05 ml, 0.061 mole). The resulting mixture is heated with oil bath to temperature of 125° C. and is stirred for 15 h. The released HCl and $SO_2$ gases are scrubbed with aqueous KOH solution. The reaction mixture is concentrated at 50° C. under reduced pressure using liquid nitrogen trap for 1 h to obtain crude $CCl_3SO_2NHSO_2Cl$ intermediate in almost quantitative yield. This intermediate is transferred to a Teflon reactor under argon atmosphere and is treated with anhydrous HF (0.61 mole) at 100° C. under reflux for 8 h. The excess HF and released HCl are removed under the flow of argon at higher temperature and scrubbed with aqueous KOH solution. The crude product is distilled at reduced pressure to produce $CF_3SO_2NHSO_2F$ in good yield.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for producing fluorotrifluoromethylsulfonyl imide (FTFSI) from a non-fluoro halogenated trihalomethylsulfonyl imide compound of the formula:

$$X^1-SO_2-NR^1-SO_2-C(X^2)_3 \qquad I$$

wherein
  $X^1$ is non-fluoro halide;
  each of $X^2$ is independently halide; and
  $R^1$ is hydrogen, alkyl, or a nitrogen protecting group;
said method comprising reacting said non-fluoro halogenated trihalomethylsulfonyl imide compound with hydrogen fluoride under conditions sufficient to produce FTFSI while removing $HX^1$, $HX^2$ or a combination thereof that is produced during the reaction.

2. The method according to claim 1, wherein said reaction condition comprises hydrogen fluoride refluxing condition.

3. The method according to claim 2, wherein said reaction condition comprises an ambient pressure condition.

4. The method according to claim 1, wherein $X^1$ and $X^2$ are Cl.

5. The method according to claim 1, wherein at least 2 equivalent of total hydrogen fluoride relative to said non-fluoro halogenated trihalomethylsulfonyl imide compound is added to the reaction.

6. The method according to claim 1, wherein the yield of FTFSI is at least 90% by weight.

7. The method according to claim 1, wherein said reaction condition comprises the presence of a catalyst.

8. The method according to claim 7, wherein said catalyst comprises a Lewis acid.

9. The method according to claim 8, wherein said Lewis acid comprises a salt of an alkaline metal, arsenic, antimony, bismuth, zinc, or a combination thereof.

10. The method according to claim 8, wherein said Lewis acid is a salt of Bi(III) compound.

11. The method according to claim 7, wherein about 0.5 equivalent or less of said catalyst is added to the reaction relative to the amount of said non-fluoro halogenated trihalomethylsulfonyl imide compound.

12. The method of claim 1 further comprising the step of producing said non-fluoro halogenated trihalomethylsulfonyl imide compound, said step comprising:
  contacting sulfamic acid with thionylhalide of the formula: $SO(X^1)_2$ under conditions sufficient to produce a reactive intermediate, wherein each $X^1$ is non-fluoro halide; and
  contacting the reactive intermediate with a trihalomethanesulfonic acid of the formula: $(X^2)_3SO_3H$ under conditions sufficient to produce said non-fluoro halogenated trihalomethylsulfonyl imide, wherein each $X^2$ is independently a non-fluoro halide.

13. The method according to claim 12, wherein $X^1$ is chloro.

14. The method according to claim 12, wherein $X^2$ is chloro.

15. The method according to claim 1, wherein $R^1$ is hydrogen.

16. A method for producing fluorotrifluoromethylsulfonyl imide (FTFSI) from a non-fluoro halogenated trihalomethylsulfonyl imide compound of the formula:

$$X^1-SO_2-NR^1-SO_2-C(X^2)_3 \qquad I$$

wherein
  $X^1$ is non-fluoro halide;
  each of $X^2$ is independently halide; and
  $R^1$ is hydrogen, alkyl, or a nitrogen protecting group;
said method comprising reacting said non-fluoro halogenated trihalomethylsulfonyl imide compound with refluxing hydrogen fluoride to produce FTFSI.

17. A method for producing fluorotrifluoromethylsulfonyl imide (FTFSI) from a (chlorosulfonyl)(trichloromethylsulfonyl)imide compound of the formula:

$$Cl-SO_2-NR^1-SO_2-CCl_3 \qquad I$$

wherein
  $R^1$ is hydrogen, alkyl, or a nitrogen protecting group;

said method comprising reacting said (chlorosulfonyl) (trichloromethylsulfonyl)imide compound with hydrogen fluoride under conditions sufficient to produce FTFSI.

18. A method for producing fluorotrifluoromethylsulfonyl imide (FTFSI) from a non-fluoro halogenated trihalomethylsulfonyl imide compound of the formula:

$$X^1-SO_2-NR^1-SO_2-C(X^2)_3 \qquad \text{I}$$

wherein
 $X^1$ is non-fluoro halide;
 each of $X^2$ is independently halide; and
 $R^1$ is hydrogen, alkyl, or a nitrogen protecting group;
said method comprising reacting said non-fluoro halogenated trihalomethylsulfonyl imide compound with hydrogen fluoride in the absence of a catalyst or in the presence of a catalyst selected from the group consisting of a salt of an alkaline metal, arsenic, antimony, bismuth, zinc, or a combination thereof, and under conditions sufficient to produce FTFSI.

* * * * *